US011536723B2

(12) United States Patent
Chia et al.

(10) Patent No.: US 11,536,723 B2
(45) Date of Patent: Dec. 27, 2022

(54) INTEGRATED IMMUNOASSAY

(71) Applicant: Mayo Foundation for Medical Education and Research, Rochester, MN (US)

(72) Inventors: Nicholas Chia, Rochester, MN (US); William A. Faubion, Rochester, MN (US); Yuguang Liu, Rochester, MN (US); Marina R. Walther-Antonio, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 608 days.

(21) Appl. No.: 16/612,851

(22) PCT Filed: May 18, 2018

(86) PCT No.: PCT/US2018/033315
§ 371 (c)(1),
(2) Date: Nov. 12, 2019

(87) PCT Pub. No.: WO2018/217553
PCT Pub. Date: Nov. 29, 2018

(65) Prior Publication Data
US 2020/0166509 A1    May 28, 2020

Related U.S. Application Data

(60) Provisional application No. 62/510,625, filed on May 24, 2017.

(51) Int. Cl.
*G01N 33/569* (2006.01)
*B01L 3/00* (2006.01)
*G01N 15/10* (2006.01)

(52) U.S. Cl.
CPC .. *G01N 33/56972* (2013.01); *B01L 3/502761* (2013.01); *G01N 15/1031* (2013.01); *G01N 15/1056* (2013.01); *B01L 2200/0652* (2013.01); *B01L 2300/0645* (2013.01); *B01L 2400/027* (2013.01); *B01L 2400/0427* (2013.01); *G01N 2015/1006* (2013.01); *G01N 2015/1081* (2013.01)

(58) Field of Classification Search
CPC ......... G01N 33/56972; G01N 15/1056; G01N 2015/1081; G01N 2015/1006; B01L 3/502761; B01L 3/5027; B01L 2400/0427; B01L 2300/0645; B01L 2200/0652
See application file for complete search history.

(56) References Cited

U.S. PATENT DOCUMENTS

2010/0101951 A1    4/2010   Tian et al.
2011/0000560 A1    1/2011   Miller et al.
2014/0248621 A1    9/2014   Collins
(Continued)

OTHER PUBLICATIONS

Chen et al., "Single-cell trapping and impedance measurement utilizing dielectrophoresis in a parallel-plate microfluidic device," Sensors and Actuators B: Chemical, Jan. 2014, 190:570-7.
(Continued)

*Primary Examiner* — Brian J. Sines
(74) *Attorney, Agent, or Firm* — Fish & Richardson P.C.

(57) ABSTRACT

Microfluidic devices and systems are provided. Methods for conducting immune assays with the devices and systems are also provided.

20 Claims, 4 Drawing Sheets

(56) References Cited

U.S. PATENT DOCUMENTS

2015/0301055 A1 10/2015 Spetzler
2016/0047735 A1 2/2016 Grisham et al.
2016/0054304 A1 2/2016 Janssen et al.

OTHER PUBLICATIONS

Cho et al., "Towards digital microfluidic circuits: creating, transporting, cutting and merging liquid droplets by electrowetting-based actuation," InTechnical Digest. MEMS 2002 IEEE International Conference. Fifteenth IEEE International Conference on Micro Electro Mechanical Systems (Cat. No. 02CH37266), Jan. 24, 2002, (pp. 32-35).
Choi et al., "Digital microfluidics. Annual review of analytical chemistry," Jul. 2012, 5:413-40.
Fair, "Digital microfluidics: is a true lab-on-a-chip possible?" Microfluidics and Nanofluidics, Jun. 2007, 3(3):245-81.
Fobel et al., "DropBot: An open-source digital microfluidic control system with precise control of electrostatic driving force and instantaneous drop velocity measurement," Applied Physics Letters, May 2013, 102(19):193513.
International Preliminary Report on Patentability in International Application No. PCT/US2018/033315 dated Dec. 5, 2019, 18 pages.
International Search Report & Written Opinion in International Application No. PCT/US2018/033315 dated Sep. 25, 2018, 23 pages.
Jebrail et al., "Digital microfluidics: a versatile tool for applications in chemistry, biology and medicine," Lab on a Chip, 2012, 12(14):2452-63.
Kopf and Zharhary, "Antibody arrays—an emerging tool in cancer proteomics," The international journal of biochemistry & cell biology, Jul. 2007, 39(7-8):1305-17.
Loftus, "Clinical epidemiology of inflammatory bowel disease: incidence, prevalence, and environmental influences," Gastroenterology, May 2004, 126(6):1504-17.
MacBeath and Schreiber, "Printing proteins as microarrays for high-throughput function determination," Science, Sep. 2000, 289(5485):1760-3.
Pollack et al., "Applications of electrowetting-based digital microfluidics in clinical diagnostics," Expert review of molecular diagnostics, May 2011, 11(4):393-407.
Shields et al., "Microfluidic cell sorting: a review of the advances in the separation of cells from debulking to rare cell isolation," Lab on a Chip, 2015, 15(5):1230-49.
Sista et al., "Development of a digital microfluidic platform for point of care testing," Lab on a Chip, Nov. 2008, 8(12):2091-104.
Sun and Morgan, "Single-cell microfluidic impedance cytometry: a review," Microfluidics and Nanofluidics, Apr. 2010, 8(4):423-43.
Chen et al., "Microfluidic Immunophenotyping Assay Platform for Immunomonitoring of Subpopulations of Immune Cells," Abstract, Presented at Proceedings of the 17th International Conference on Miniaturized Systems for Chemistry and Life Sciences, Freiburg, Germany, Oct. 27-31, 2013, 3 pages.
Green et al., "Microfluidic Immunophenotyping and Cytokine Detection for the Diagnosis of Uveitis and Ocular Cancer," Invest. Ophthalmol. Vis. Science, Apr. 2011, 52(14):418, 2 pages.
Kim et al., "Application of single-cell RNA sequencing in optimizing a combinatorial therapeutic strategy in metastatic renal cell carcinoma," Genome Biology, Apr. 29, 2016, 17:80, 17 pages.
Streets et al., "Microfluidic single-cell whole-transcriptome sequencing," Proc. Natl. Acad. Sci. USA, Apr. 29, 2014,111(19):7048-7053.

INTEGRATED IMMUNOASSAY

CROSS-REFERENCE TO RELATED APPLICATIONS

This application is a National Stage application under 35 U.S.C. § 371 of International Application No. PCT/US2018/033315, having an International Filing Date of May 18, 2018, which claims priority to U.S. Application Ser. No. 62/510,625, filed on May 24, 2017. The disclosures of the prior applications are considered part of the disclosure of this application, and are incorporated in their entirety into this application.

TECHNICAL FIELD

This document relates to immune assays on digital microfluidic devices, devices and systems for carrying out the immune assays, and methods of conducting immune assays.

BACKGROUND

Human immune mediated diseases (e.g., Multiple Sclerosis, Rheumatoid Arthritis, Crohn's Disease, Inflammatory Bowel Disease) affect nearly 1 in 31 of the U.S. population. See Loftus, Gastroenterology, 2004 May; 126(6):1504-17. Such diseases often present complicated and non-uniform prognoses; while aggressive and devastating in some patients, immune mediated diseases may be mild and indolent in others. Current prognostic tools such as anti-microbial serology and patient genotyping are unable to consistently predict the variability of disease behavior and reveal only limited insight into the established genetic risk variants. In addition, no tools are currently available to predict therapeutic response to classes of drugs. Despite these diagnostic and prognostic deficiencies, and the remarkable prevalence of immune mediated diseases, no robust assay of immune response exists.

SUMMARY

One reason for the gap in mechanistic insight is the focus on genotype in the absence of additional key disease driving factors such as the phenotypic immune response. Therefore, there is a need to develop new immune phenotyping approaches capable of prospectively identifying homogenous disease subtypes with predictable outcomes, such as response to therapy or risk of disease progression. The ability to define the molecular pathways driving variable disease behavior may lead to significant insight into prognosis, therapeutic response, and basic pathophysiology of immune mediated disease. Understanding the complex biological system of the immune response can involve a multiparameter data generation and analysis strategy that integrates components of the immune response gathered on a single blood sample from the same genotyped patient. Thus, there is a need for an integrated assay for profiling single immune cells at the level of cellular identity, signal transduction, and gene expression.

In one aspect, a method is provided for determining an immunological phenotype of a plurality of white blood cells in a sample comprising: (a) introducing a sample comprising a plurality of white blood cells into a sample reservoir of a microfluidic device; (b) dispensing, by electromechanical droplet manipulation, a droplet of the sample comprising a cell from the sample reservoir into a channel operably connected to the sample reservoir; (c) moving the droplet, by electromechanical droplet manipulation, along the channel to a first immobilization electrode; (d) determining whether or not the cell is immobilized on the first immobilization electrode; (e) determining a subtype of the cell based on step (d); (f) moving the droplet comprising the cell, by electromechanical droplet manipulation, from the first immobilization electrode along a channel in a direction based on the subtype of the cell determined in step (d); (g) determining a final phenotypic subtype of the cell; and (h) moving the droplet comprising the cell, by electromechanical droplet manipulation, along a channel to a cell collection reservoir based on such final phenotypic subtype of the cell determined in step (g). The method can further comprise (i) repeating steps (b)-(h) for a second droplet of the sample, wherein the second droplet comprises a cell. Step (g) of the method can comprise determining whether or not the cell is immobilized on one or more immobilization electrodes. The method can further comprise (j) independently collecting cells of one or more subtypes to create one or more pools of cells having the same subtype. The method can further comprise (k) lysing one or more pools of cells having the same subtype to release cellular contents.

In another aspect, a microfluidic device is provided comprising a first substrate; a second substrate; and a fluid layer disposed between the first substrate and the second substrate. The fluid layer can comprise a first sample reservoir; a first reagent reservoir; a first cell collection reservoir; a second cell collection reservoir; a channel network connecting the first and second reservoirs; and an electrode layer disposed between the first substrate and the fluid layer. The electrode layer can comprise a first immobilization electrode aligned within a first portion of the channel network of the fluid layer, wherein the first immobilization electrode is configured to immobilize a cell having a first target surface marker, wherein the first portion of the channel network is positioned between the sample reservoir and each of the first cell collection reservoir and the second cell collection reservoir. Each immobilization electrode can comprise an immobilized antibody specific to a cell surface marker.

In another aspect, a microfluidic device is provided that is configured to concurrently identify, from a single sample of white blood cells, two or more cell subtypes selected from CD4 positive alpha beta cells, CD4 positive gamma delta cells, CD8 positive alpha beta cells, CD8 positive gamma delta cells, NK cells, mature B cells, naïve B cells, HLA positive cells, HLA-DR positive cells, and dendritic cells. The microfluidic device can be further configured to quantify the number of cells in each of the two or more cell subtypes.

In another aspect, a system is provided comprising a microfluidic device as described herein; a control circuit; a power supply; and a graphical user interface.

In another aspect, a method is provided for analyzing, independently, the RNA of a single cell subtype in a sample comprising a plurality of cell subtypes comprising: (a) splitting the sample into one or more cell subtypes by passing at least a portion of the sample through a microfluidic device to create one or more pools of cells having the same subtype; (b) lysing one or more pools of cells having the same subtype to release cellular contents; (c) separating the cellular contents into an RNA component and a cellular protein component; and (d) analyzing the RNA component.

In another aspect, a method is provided for analyzing signal transduction proteins of a single cell subtype in a sample comprising a plurality of cell subtypes comprising: (a) splitting the sample into one or more cell subtypes by passing at least a portion of the sample through a microfluidic device to create one or more pools of cells having the same subtype; (b) lysing one or more pools of cells having the same subtype to release cellular contents; (c) separating the cellular contents into an RNA component and a cellular protein component; and (d) analyzing the cellular protein component.

In another aspect, a method is provided for determining a disease phenotype of an immune mediated disease in a patient having the immune mediated disease comprising: (a) splitting the sample into one or more cell subtypes by passing at least a portion of the sample through a microfluidic device to create one or more pools of cells having the same subtype; (b) lysing one or more pools of cells having the same subtype to release cellular contents; (c) separating the cellular contents into an RNA component and a cellular protein component; (d) analyzing at least one of the RNA component and the cellular protein component; and (e) determining the disease phenotype based on step (d). The immune mediated disease can be selected from Crohn's disease, multiple sclerosis, rheumatoid arthritis, and inflammatory bowel disease.

In another aspect, a method is provided for determining an immunological phenotype of a plurality of white blood cells in a sample comprising: (a) identifying a cell subtype for each of two or more of the white blood cells; (b) quantifying each cell subtype; (c) isolating and pooling cells of each subtype into one or more subtype pools; (d) lysing cells of each of the one or more subtype pools to yield one or more cellular content pools; (e) separating the cellular content pools of each cell subtype into an RNA component and a protein component; and (f) analyzing at least one of the RNA component and the protein component.

In another aspect, a microfluidic device is provided comprising: at least one sample reservoir; a first channel operably connect to the sample reservoir; a first electrode disposed within the first channel and downstream of the sample reservoir; a second channel; a third channel; a first channel junction disposed downstream of the first electrode and connecting the first channel to at least the second channel and the third channel; a second electrode disposed downstream of the first electrode and at or upstream of the first channel junction; a fourth channel; a fifth channel; a second channel junction disposed downstream of the first channel junction and connecting the second channel to at least the fourth channel and the fifth channel; a third electrode disposed downstream of the first channel junction and at, upstream of, or downstream and adjacent to the second channel junction, wherein when the third electrode is disposed downstream and adjacent to the second channel junction, the third electrode is disposed within the fifth channel; a fourth electrode disposed downstream of the first channel junction and at, upstream of, or downstream and adjacent to the second channel junction, wherein when the fourth electrode is disposed downstream and adjacent to the second channel junction, the fourth electrode is disposed within the fourth channel; a sixth channel; a seventh channel; a third channel junction disposed downstream of the second channel junction and connecting the fourth channel to at least the sixth channel and the seventh channel; a fifth electrode disposed at or upstream of the third channel junction and downstream of the second channel junction; and a first cell collection reservoir connected to the sixth channel and disposed downstream of the third channel junction.

The assays, devices, systems, and methods described herein can provide several advantages. These tools and methods can define the immunological fingerprint associated with clinical phenotypes (e.g., severe or mild) of patients with immune mediated diseases. In some embodiments phenotyping can include gene expression, signal transduction, identification of one or more cell surface markers, quantification of cells having target surface markers, or quantification of target surface markers on a given cell. The assays can provide specific quantification of immune cells, cell surface immune phenotyping, single cell RNA analysis, and analysis of signal transduction pathways involved in the manifestation of the diseases. This data can provide identification of patients at higher risk for severe disease and future disability, thus identifying which patients may require more aggressive treatment. Identifying precise immune pathways associated with severe and mild disease can guide the development of individualized therapies with improved, predictable, and cost-effective outcomes.

Unless otherwise defined, all technical and scientific terms used herein have the same meaning as commonly understood by one of ordinary skill in the art to which this invention pertains. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

For the terms "for example" and "such as," and grammatical equivalences thereof, the phrase "and without limitation" is understood to follow unless explicitly stated otherwise. As used herein, the term "about" is meant to account for variations due to experimental error. As used herein, the singular forms "a," "an," and "the" are used interchangeably and include plural referents unless the context clearly dictates otherwise.

Also herein, the recitations of numerical ranges by endpoints include all numbers subsumed within that range (e.g., 1 to 5 includes 1, 1.5, 2, 2.75, 3, 3.80, 4, 5, etc.).

Other features and advantages of the invention will be apparent from the following detailed description and figures, and from the claims.

DESCRIPTION OF DRAWINGS

Like reference symbols in the various drawings indicate like elements.

DETAILED DESCRIPTION

This document provides integrated immune assays using digital microfluidic technology, digital microfluidic devices for carrying out the assays, and methods of carrying out the assays. The integrated immune assays can provide diagnostic and prognostic insight into the manifestation and treatment of an immune mediated disease (e.g., Crohn's Disease, Multiple Sclerosis, Rheumatoid Arthritis, Inflammatory Bowel Disease) in an individual subject. The assays described herein can be used to measure multiple components of an immune response at the single cell level using a peripheral blood sample from a single patient. The assays can concurrently sort identify one or more cell subtypes in a sample having a plurality of cells while providing parallel assays including, for example, quantification of cells and cell subtypes, RNA analysis and signal transduction protein analysis, thus providing phenotypic information. The assays described herein can provide an immunologic fingerprint associated with clinical phenotypes of immune mediated diseases and determine whether a patient exhibits severe or indolent immune mediated disease, identify patients at highest risk of future disability that require the most aggressive treatment, and guide the development of individualized therapies with improved, predictable, and cost-effective outcomes.

Figure 1:
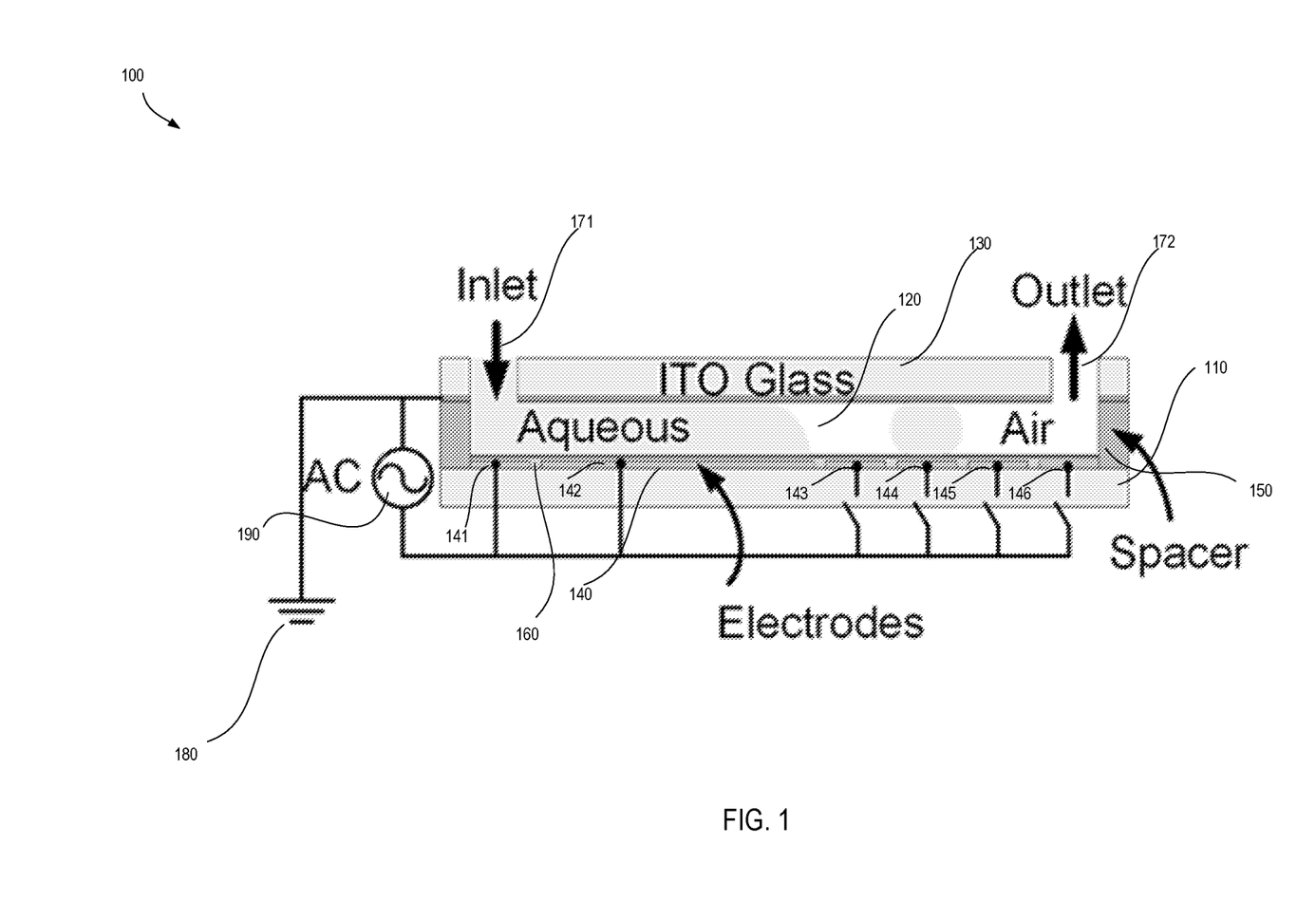
FIG. 1 is a cross sectional view of a digital microfluidic device according to one embodiment provided herein.
Figure 2A:
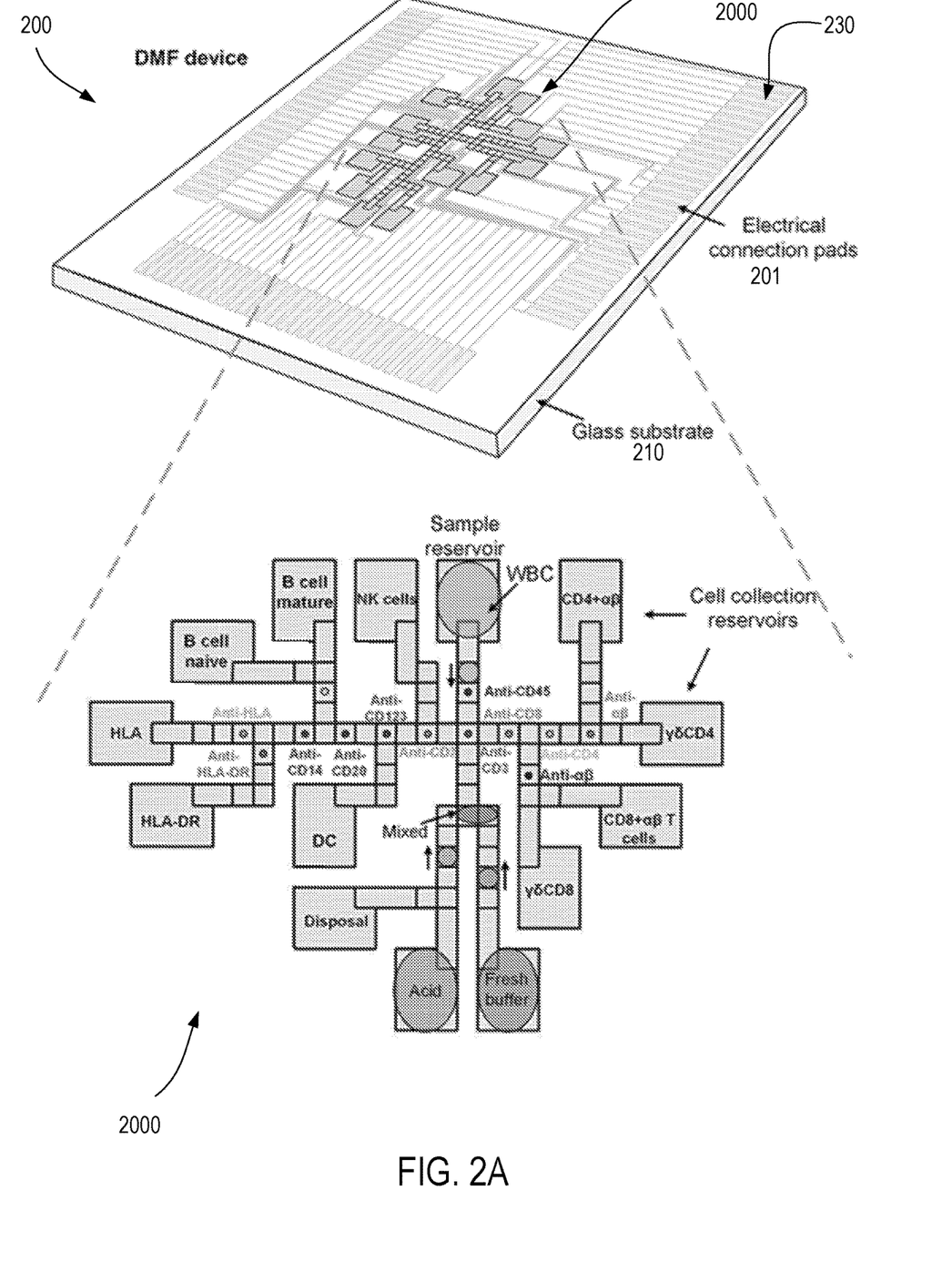
FIG. 2A is a perspective view of an embodiment of a digital microfluidic device with a magnified view of an embodiment of a microfluidic channel network and electrode array according to one embodiment provided herein.
Figure 2B:
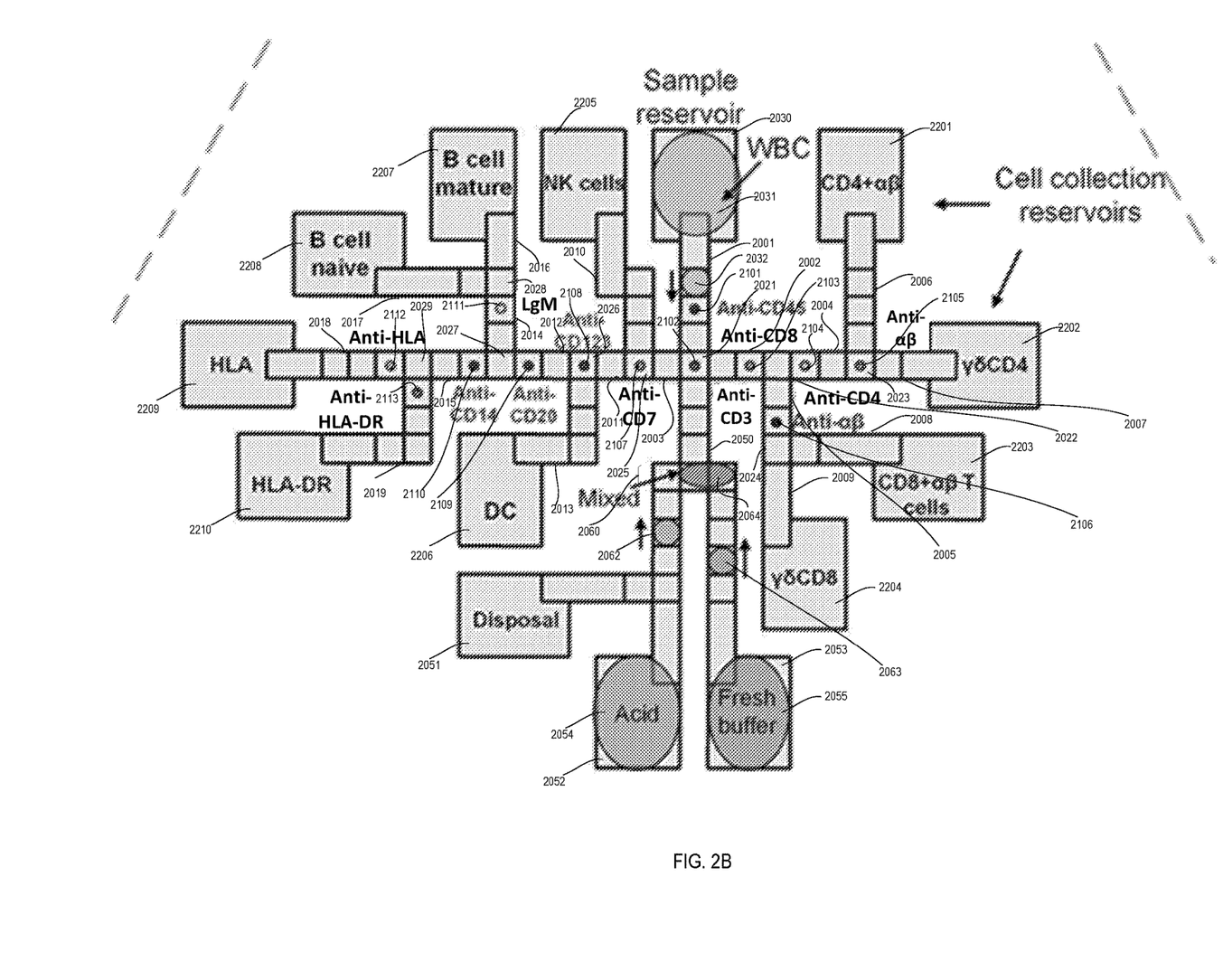
FIG. 2B is a further magnified view of the microfluidic channel network and electrode array of the digital microfluidic device of FIG. 2A.

In some embodiments, as shown in exemplary device 100 in FIG. 1, the integrated immune assays disclosed herein can include using digital microfluidic devices having a first substrate (110), a fluid layer (120), and a second substrate (130). The devices described herein can further include an electrode layer (140) disposed between the first substrate (110) and the fluid layer (120). In some embodiments, the first substrate (110) can be, for example, a glass slide coated with indium tin oxide (ITO) as a transparent conductive electrode layer (140). In some embodiments, the first substrate can include non-transparent conductive materials, such as metal coated slides. The electrodes layout, such as depicted in FIGS. 2A and 2B, can be patterned on the first substrate to form ITO electrodes and electrical connections. In some embodiments, a spacer layer (150) is patterned around the edges of the first substrate. The spacer layer can, in some embodiments, define the device height, channel height, fluid layer height, or a combination thereof. Exemplary methods of creating the spacer layer (150) include using a negative photoresist, such as SU-8 or PEMX, to form physical boundaries of the fluid layer. Alternatively, in some embodiments, thin films such as polymer sheets or adhesive layers can be used to create the physical boundaries. An insulativehn layer (160) can be disposed between the electrode layer (140) and the fluid layer (120) to insulate the electrodes (140). Some exemplary insulative layers can include Parylene C, Parylene HT, SU-8 photoresists, polydimethylsiloxane, $Al_2O_3$, silicon nitride, or any dielectric layer. The thickness of the insulative layer can vary based on material properties and voltage required. In some embodiments, the insulative layer can be 5 µm thick. In some embodiments, the second substrate (130) can be, for example, a glass or a glass microscope coverslip. In some embodiments, the second substrate (130) can be coated with ITO or other conductive material to provide electrical ground. The first and second substrates can be coated with a hydrophobic layer to adjust the contact angle of the glass surfaces as necessary.

In some embodiments, a hydrophobic layer can be spin-coated on both the first and second substrates so that all glass surfaces have a contact angle of about 110° without applied voltage in ambient air. Exemplary hydrophobic layers can include fluoropolymer-based or perfluoroalkyl copolymer-based products, such as TEFLON AF 1600. In some embodiments, the hydrophobic layer can be from about 10 to about 1000 nm thick. In some embodiments, the hydrophobic layer is about 50 nm thick. In some embodiments, a microscale hydrophilic circle can be fabricated in the middle of selected electrodes and cell-specific antibodies can be pre-immobilized in these circles. The hydrophilic circles can be created using lift-off microfabrication methods, or any other suitable method. In some embodiments, cell-specific antibodies can be immobilized on the circles using printing techniques such as those described in MacBeath, et al., Science, vol. 289, no. 5485, pp. 1760-1763, 2000; and Kopf, et al., The International Journal of Biochemistry & Cell Biology, vol. 39, no. 7, pp. 1305-1317, 2007, which are incorporated herein by reference, through modification of substrate surface chemistry that enables the binding of the capture antibodies such as to glass, or any other suitable method.

In some embodiments, the first and second substrates are bonded together using a suitable adhesive, e.g., UV-curable epoxy, to form the fluid layer (120) between the first substrate and the second substrate, for fluid manipulation, with all four sides sealed by the spacer layer and the adhesive. The fluid layer makes up the channel network through which sample droplets pass. In some embodiments, at least one inlet (171) or aperture perforating one of the first and second substrates is provided and allows for, e.g., input of the sample and/or reagents such as acid or buffer. In some embodiments, at least one outlet (172) or aperture perforating one of the first and second substrates is provided and allows for, e.g., removal of waste and removal of specific cell subtypes for further analysis.

In the microfluidic devices described herein, the electrodes (e.g., 141, 142, 143, 144, 145, 146) can be connected in a circuit (180) powered by power supply (190). Selected electrodes can be pre-immobilized with monoclonal antibodies specific for the surfaces of target cells. In some embodiments, fluid, e.g., sample fluid, can be directed and manipulated based on applied electrical potential, known as electrowetting or electromechanical droplet manipulation, as described in, for example, Sista, et al., Lab on a Chip, vol. 8, no. 12, pp. 2091-2104, 2008; Pollack, et al. Expert review of molecular diagnostics, vol. 11, no. 4, pp. 393-407, 2011, and Cho, et al. S.-K. Fan, H. Moon, and C.-J. Kim, "Towards digital microfluidic circuits: creating, transporting, cutting and merging liquid droplets by electrowetting-based actuation." pp. 32-35, which are incorporated herein by reference. Discrete droplets can be manipulated individually in a programmed manner including droplet transport, mixing and merging without the need for mechanical moving parts. Microliter to picoliters of droplets can be manipulated and droplet-based functions can be performed according to real time needs. A droplet of white blood cells (WBC) can be dispensed onto a sample reservoir in the devices, and a droplet of the cells can be dispensed from the reservoir by splitting and move across the electrode arrays. Cells in the droplet can be captured by their specific antibodies pre-immobilized on the electrodes. Impedance measurements can be used as for quantification of each cell subtype and to determine whether or not a cell is captured by the antibodies immobilized on each electrode. Exemplary methods for conducting impedance measurements include those described in Sun et al., Microfluidics and Nanofluidics, vol. 8, no. 4, pp. 423-443, 2010; Shields I V et al., Lab on a Chip, vol. 15, no. 5, pp. 1230-1249, 2015; and Chen, et al., Sensors and Actuators B: Chemical, vol. 190, pp. 570-577, 2014, which are incorporated herein by reference.

In some embodiments, microfluidic devices described herein include a first substrate; a second substrate; and a fluid layer disposed between the first substrate and the second substrate. The fluid layer can, in some embodiments, include a first sample reservoir; a first reagent reservoir; a first cell collection reservoir; a second cell collection reservoir; a channel network connecting the reservoirs; and an electrode layer disposed between the first substrate and the fluid layer. In some embodiments, the electrode layer can include a first immobilization electrode aligned within a first portion of the channel network of the fluid layer, wherein the first immobilization electrode is configured to immobilize a cell having a first target surface marker, wherein the first portion of the channel network is positioned between the sample reservoir and each of the first cell collection reservoir and the second cell collection reservoir. In some embodiments, the first immobilization electrode includes immobilized anti-CD45 antibody. The devices may, in some embodiments, further include one or more electrodes selected from an electrode having immobilized anti-CD3 antibody, an electrode having immobilized anti-CD8 antibody, an electrode having immobilized anti-CD4 antibody, an electrode having immobilized anti-αβ antibody, an electrode having immobilized anti-CD7 antibody, an electrode having immobilized anti-CD123 antibody, an electrode having immobilized anti-CD20 antibody, an electrode having immobilized anti-CD14 antibody, an electrode having immobilized anti-LgM antibody, an electrode having immobilized anti-HLA antibody, and an electrode having immobilized anti-HLA-DR antibody.

In general, the digital microfluidic devices described herein can be controlled by a software system operated through a graphical user interface (GUI). In some embodiments, a software system such as that described in Fobel et al., Applied Physics Letters, vol. 102, no. 19, pp. 193513, 2013, and incorporated herein by reference, can be used, with appropriate modifications made for the particular design of a given microfluidic device. In some embodiments, a customized clamp with metal pads can connect the devices with the control circuitry powered by an AC power supply. In some exemplary embodiments, the control system can have the functionality to switch on and off individual electrodes in the digital microfluidic devices in a programmed fashion through the GUI, thus allowing for programmable droplet manipulation and automated processes. In some embodiments, an impedance-sensing mechanism can be incorporated into the circuitry for the detection of single cells' attachment to the surface of the electrodes and quantification of the cells. In some embodiments, a system is provided. The system can include a microfluidic device described herein; a control circuit; a power supply; and a graphical user interface.

FIG. 2A shows a perspective view of an embodiment of a digital microfluidic device (200) with a magnified view of an embodiment of an electrode array schematic and microfluidic channel network (2000) that defines an exemplary fluid layer. In some embodiments, the device can have a first substrate (210) and a second substrate (230), and have a fluid layer defined by a microfluidic channel network (2000) having an electrode array disposed therein, with electrical connection pads (201) providing a link to the circuitry for operating the device. In some embodiments, the electrical connection pads can serve as the interface between the device and the power supply, such that the voltage passes from the power supply through the electrical connection pads. Thin-film transistor (TFT) based and active matrix thin-film transistor (AM-TFT) based electrowetting devices may also be used in the devices and methods described herein.

FIG. 2B shows a further magnification of the microfluidic channel network and electrode array of the exemplary digital microfluidic device of FIG. 2A. In the depicted embodiment, the device has a sample reservoir (2030) for injecting and holding a sample, such as a patient's white blood cells. In some embodiments, the devices can have more than one sample reservoir. The device further includes a first channel (2001) operably connected to the sample reservoir (2030); a first electrode (2101) disposed within the first channel (2001) and downstream of the sample reservoir (2030). In some embodiments, the first electrode can have anti-CD45 antibody immobilized on its surface. In some embodiments, all leukocytes to be subsequently characterized are CD45 positive. In some embodiments, all cells that are CD45 negative, such as platelets or red blood cells, will be moved to a waste or disposal reservoir (2051).

The exemplary device further includes a second channel (2002) and a third channel (2003), as well as a first channel junction (2021) disposed downstream of the first electrode (2101) and connecting the first channel (2001) to at least the second channel (2002) and the third channel (2003). A second electrode (2102) is disposed downstream of the first electrode (2101) and at the first channel junction (2021). In some embodiments, the second electrode can be disposed upstream of the first channel junction (2021). In some embodiments, the second electrode (2102) can have anti-CD3 antibody immobilized on its surface.

The device further includes a fourth channel (2004), a fifth channel (2005), and a second channel junction (2022) disposed downstream of the first channel junction (2021) and connecting the second channel (2002) to at least the fourth channel (2004) and the fifth channel (2005). A third electrode (2103) is disposed downstream of the first channel junction (2021) and upstream of the second channel junction (2022). In some embodiments, the third electrode (2103) is disposed at or downstream and adjacent to the second channel junction (2022). In some embodiments, when the third electrode (2103) is disposed downstream and adjacent to the second channel junction (2022), the third electrode (2103) is disposed within the fifth channel (2005). In some embodiments, the third electrode can have anti-CD8 antibody immobilized on its surface.

The exemplary device further includes a fourth electrode (2104) disposed downstream of the first channel junction (2021), downstream and adjacent to the second channel junction (2022), and within the fourth channel (2004). In some embodiments, the fourth electrode (2104) can be disposed at or upstream of the second channel junction (2022). In some embodiments, the fourth electrode (2104) can have anti-CD4 antibody immobilized on its surface.

The exemplary device of FIG. 2B further includes a sixth channel (2006), a seventh channel (2007), and a third channel junction (2023) disposed downstream of the second channel junction (2022) and connecting the fourth channel (2004) to at least the sixth channel (2006) and the seventh channel (2007). A fifth electrode (2105) is disposed at the third channel junction (2023) and downstream of the second channel junction (2022). In some embodiments, the fifth electrode (2105) can be disposed upstream of the third channel junction (2023) and downstream of the second channel junction (2022). In some embodiments, the fifth electrode (2105) can have anti-αβ antibody immobilized on its surface. A first cell collection reservoir (2201) can be connected to the sixth channel (2006) and disposed downstream of the third channel junction (2023). A second cell collection reservoir (2202) can be connected to the seventh channel (2007) and disposed downstream of the third channel junction (2023).

Cell collection reservoirs can be present for collecting and pooling cells of a specific subtype once a desired phenotypic identification has been reached. The cell collection reservoirs can serve as waste reservoirs, or as collection units for further analysis of the cells. In some embodiments, a cell collection reservoir is operably connected to an outlet, which can serve as a route to remove phenotyped cells for further analysis or waste, or to introduce reagents for further cellular analysis within the cell collection reservoir. In some embodiments, the fluid in the collection reservoir will be collected for further analysis by pipetting through an outlet, such as a hole pre-drilled on the top substrate. In some embodiments, the cell collection reservoirs can be pre-loaded with analytical substrates or reagents for further analyzing the cell population that reaches the specific cell collection reservoir. In some embodiments, additional electrodes can be disposed upstream of the cell collection reservoirs. In some embodiments, additional electrodes can be disposed downstream of the cell collection reservoirs so that the cells in the collection reservoir can be moved onto additional electrode arrays for further analyses.

The exemplary device of FIG. 2B further includes a fourth channel junction (2024) disposed downstream of the second channel junction (2022) and connecting the fifth channel (2005) to at least the eighth channel (2008) and the ninth channel (2009). A sixth electrode (2106) is disposed upstream of the fourth channel junction (2024) and downstream of the second channel junction (2022). In some embodiments, the sixth electrode (2106) is disposed at the fourth channel junction (2024). In some embodiments, the sixth electrode can have anti-αβ antibody immobilized on its surface. A third cell collection reservoir (2203) can be connected to the eighth channel (2008) and disposed downstream of the fourth channel junction (2024). A fourth cell collection reservoir (2204) can be connected to the seventh channel (2007) and disposed downstream of the fourth channel junction (2024).

The device further includes a tenth channel (2010), an eleventh channel (2011), and a fifth channel junction (2025) disposed downstream of the second electrode (2102) and connecting the third channel (2003) to at least the tenth channel (2010) and the eleventh channel (2011). A seventh electrode (2107) is disposed downstream of the first channel junction (2021) and at the fifth channel junction (2025). In some embodiments, the seventh electrode (2107) is disposed upstream of the fifth channel junction (2025). In some embodiments, the seventh electrode (2107) can have anti-CD7 antibody immobilized on its surface. A fifth cell collection reservoir (2205) can be connected to the tenth channel (2010) and disposed downstream of the fifth channel junction (2025).

The exemplary device further includes a twelfth channel (2012), a thirteenth channel (2013), and a sixth channel junction (2026) disposed downstream of the seventh electrode (2107) and connecting the eleventh channel (2011) to at least the twelfth channel (2012) and the thirteenth channel (2013). An eighth electrode (2108) is disposed downstream of the fifth channel junction (2025) and at the sixth channel junction (2026). In some embodiments, the eighth electrode (2108) is disposed upstream of the sixth channel junction (2026). In some embodiments, the eighth electrode (2108) can have anti-CD123 immobilized on its surface. A sixth cell collection reservoir (2206) can be connected to the thirteenth channel (2013) and disposed downstream of the sixth channel junction (2026).

The device further includes a fourteenth channel (2014), a fifteenth channel (2015), and a seventh channel junction (2027) disposed downstream of the sixth channel junction (2026) and connecting the twelfth channel (2012) to at least the fourteenth channel (2014) and the fifteenth channel (2015). A ninth electrode (2109) is disposed downstream of the sixth channel junction (2026) and upstream of the seventh channel junction (2027). In some embodiments, the ninth electrode (2109) is disposed downstream and adjacent to the seventh channel junction (2027) and within the fifteenth channel (2015). In some embodiments, the ninth electrode (2109) can have anti-CD20 antibody immobilized on its surface. A tenth electrode (2110) is disposed downstream of the sixth channel junction (2026), downstream and adjacent to the seventh channel junction (2027), and disposed within the fifteenth channel (2015). In some embodiments, the tenth electrode (2110) can be disposed at or upstream of the sixth channel junction (2026). In some embodiments, the tenth electrode (2010) can have anti-CD14 antibody immobilized on its surface.

The exemplary device of FIG. 2B further includes a sixteenth channel (2016), a seventeenth channel (2017), and an eighth channel junction (2028) disposed downstream of the seventh channel junction (2027) and connecting the fourteenth channel (2014) to at least the sixteenth channel (2016) and the seventeenth channel (2017). An eleventh electrode (2111) is disposed downstream of the seventh channel junction (2027) and upstream of the eighth channel junction (2028). In some embodiments, the eleventh electrode (2111) can be disposed at the eighth channel junction (2028). In some embodiments, the eleventh electrode (2111) can have anti-IgM antibody immobilized on its surface. A seventh cell collection reservoir (2207) can be connected to the sixteenth channel (2016) and disposed downstream of the eighth channel junction (2028). An eighth cell collection reservoir (2208) can be connected to the seventeenth channel (2017) and disposed downstream of the eighth channel junction (2028).

The device further includes an eighteenth channel (2018), a nineteenth channel (2019), and a ninth channel junction (2029) disposed downstream of the seventh channel junction (2027) and connecting the fifteenth channel (2015) to at least the eighteenth channel (2018) and the nineteenth channel (2019). A twelfth electrode (2112) is disposed downstream of the seventh channel junction (2027), downstream and adjacent to the ninth channel junction (2029), and within the eighteenth channel (2018). In some embodiments, the twelfth electrode (2112) can be disposed at or upstream of the ninth channel junction (2029). In some embodiments, the twelfth electrode (2112) can have anti-HLA antibody immobilized on its surface. A thirteenth electrode (2113) is disposed downstream of the seventh channel junction (2027), downstream and adjacent to the ninth channel junction (2029), and within the nineteenth channel (2019). In some embodiments, the thirteenth electrode (2113) can be disposed at or upstream of the ninth channel junction (2029). In some embodiments, the thirteenth electrode (2113) can have anti-HLA-DR antibody immobilized on its surface. A ninth cell collection reservoir (2209) can be connected to the eighteenth channel (2018) and disposed downstream of the ninth channel junction (2029). A tenth cell collection reservoir (2210) can be connected to the nineteenth channel (2019) and disposed downstream of the ninth channel junction (2029).

In some embodiments, the devices can include one or more alternate reservoirs operatively linked to at least a portion of any one of the channels of the device. In some embodiments, such as the embodiment of FIG. 2B, the devices can include one or more alternate reservoirs operatively linked to at least a portion of any one of the first through nineteenth channels by a twentieth channel (2050). In some embodiments, the at least one alternate reservoir can be selected from a disposal reservoir, a first reagent reservoir, a second reagent reservoir, and combinations thereof. In some embodiments, a reagent reservoir can include an acid reservoir and a buffer reservoir. In some embodiments, the devices can include a disposal reservoir, a first reagent reservoir, and a second reagent reservoir. In some embodiments, the devices can include a disposal reservoir (2051), an acid reservoir (2052), and a buffer reservoir (2053). In some embodiments, the acid reservoir (2052) can contain an acid (2054) for dispensing into the channel network. In some embodiments, the buffer reservoir (2053) can contain a buffer (2055) for dispensing into the channel network. In some embodiments, the devices can include a mixing zone operatively connected to at least one channel of the devices in which reagents such as acid and buffer can be mixed as needed on board the devices. In some embodiments, the acid reservoir and the buffer reservoir are each independently connected to a mixing zone (2060), allowing mixing and dilution of the reagents during the assay as needed. In some embodiments s droplet of acid (2062) is split from the acid (2054) in the acid reservoir (2052) and moved along a channel via electromechanical manipulation to a mixing zone (2060), a droplet of buffer (2063) is split from the buffer (2055) in the buffer reservoir (2053) and moved along a channel via electromechanical manipulation to a mixing zone (2060), where the droplets are merged into a single reagent droplet (2064) before entering the rest of the channel network.

The flow of the immune assays described herein is, in some embodiments, analogous to a decision tree. The strategy of cell flow and the definition of cell subsets for one exemplary embodiment of an immune assay described herein are demonstrated in FIG. 3. The operation of the device depicted in FIGS. 2A and 2B follows the decision tree of FIG. 3, however, the basic ideas of design and methodology of the assays described herein can be applied to a wide range of applications based on the desired phenotype identification and choice of needed antibodies.

Figure 3:
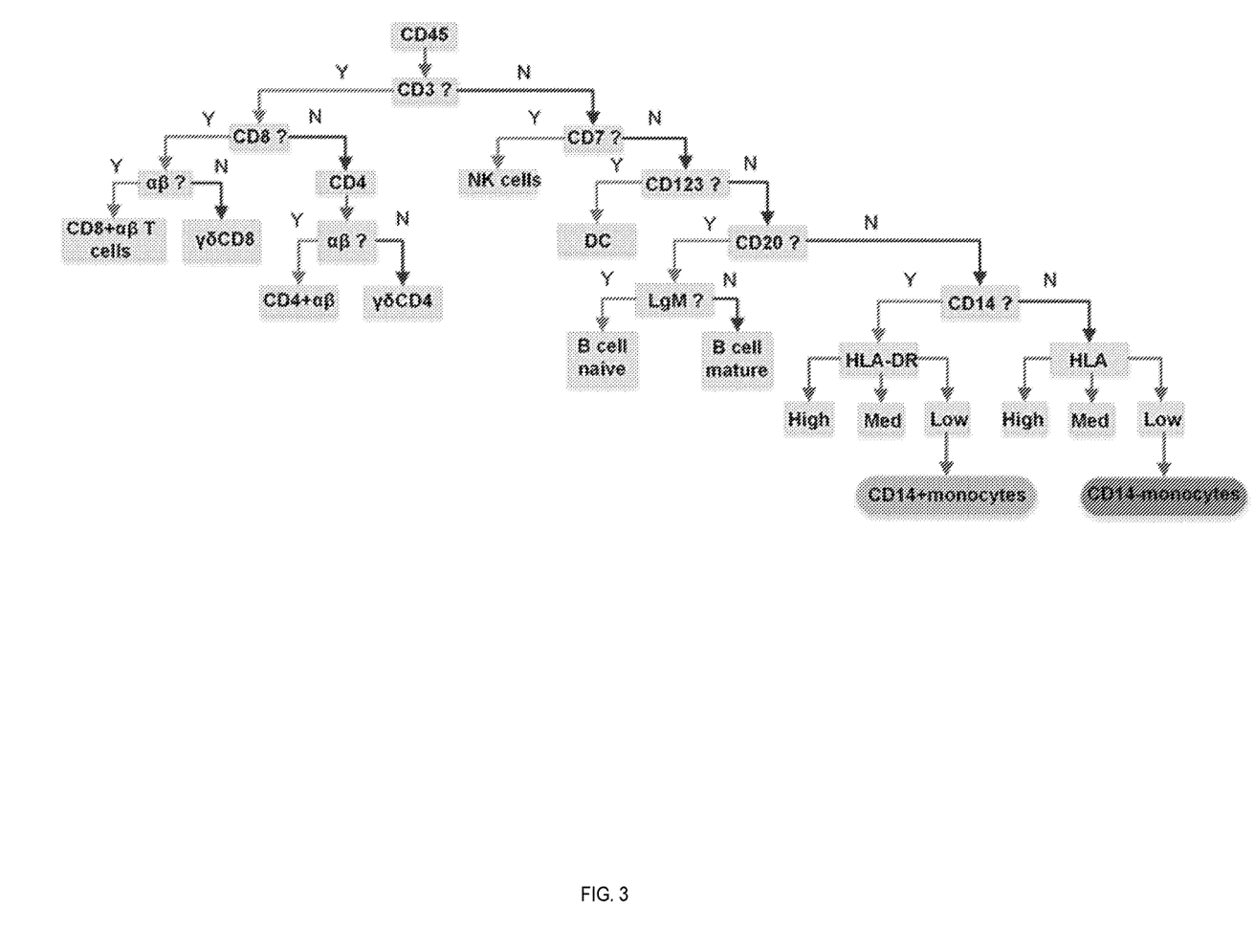
FIG. 3 is a schematic of a decision tree depicting the operation of one embodiment provided herein.

In the exemplary assay of FIG. 3, a first level of identification, representative of the first electrode (2101) of FIG. 2B, interrogates a cell or cells in a droplet for the presence CD45. Assuming CD45 is present, the cell or cells are next interrogated at a second level of identification for the presence of CD3, representative of the second electrode (2102). If CD3 is present, the cell or cells are next interrogated at a third level of identification for the presence of CD8, representative of the third electrode (2103). If CD3 is not present at the second level of identification, the cell or cells are next interrogated at a third level of identification for the presence of CD7, representative of the seventh electrode (2107).

Turning first in FIG. 3 to an embodiment where a cell population expresses CD3, the cell or cells are next interrogated at a third level of identification for the presence of CD8, representative of the third electrode (2103). If CD8 is present, the cell or cells are next interrogated at a fourth level of identification for the presence of a T cell receptor (TCR) for antigen $\alpha\beta$, representative of the sixth electrode (2106). If CD8 is not present, the cel or cells are next interrogated at a fourth level of identification for the presence of CD4, representative of the fourth electrode (2104).

Turning in FIG. 3 to an embodiment in which a cell population that expresses CD8, the cell or cells are next interrogated at a fourth level of identification for the presence of TCR $\alpha\beta$, representative of the sixth electrode (2106). If TCR $\alpha\beta$ is present, the cell population has reached its final point of cell surface phenotyping for the exemplary assay and the cell or cells are identified as CD8 positive $\alpha\beta$ T cells and can be stored in the third cell collection reservoir (2203) and further analyzed based on that identification. If TCR $\alpha\beta$ is not present, the cell population has reached its final point of cell surface phenotyping for the exemplary assay and the cell or cells are identified as TCR $\delta\gamma$ CD8 positive T cells and can be stored in the fourth cell collection reservoir (2204) and further analyzed based on that identification.

Turning in FIG. 3 to an embodiment in which a cell population that does not express CD8 at the third level of identification, the cell or cells are next interrogated at a fourth level of identification for the presence of CD4, representative of the fourth electrode (2104). If CD4 is present, the cell or cells are next interrogated at a fifth level of identification for the presence of TCR $\alpha\beta$, representative of the fifth electrode (2105), which can, in some embodiments, quantify the cells. If TCR $\alpha\beta$ is present, the cell population has reached its final point of cell surface phenotyping for the exemplary assay and the cell or cells are identified as CD4 positive TCR $\alpha\beta$ T cells and can be stored in the first cell collection reservoir (2201) and further analyzed based on that identification. If TCR $\alpha\beta$ is not present, the cell population has reached its final point of cell surface phenotyping for the exemplary assay and the cell or cells are identified as TCR $\delta\gamma$ CD4 positive T cells and can be stored in the second cell collection reservoir (2202) and further analyzed based on that identification.

Turning next in FIG. 3 to an embodiment in which a cell population does not express CD3 at the second level of identification, the cell or cells are next interrogated at a third level of identification for the presence of CD7, representative of the seventh electrode (2107). If CD7 is present, the cell population has reached its final point of cell surface phenotyping for the exemplary assay and the cell or cells are identified as natural killer (NK) cells and can be stored in the fifth cell collection reservoir (2205) and further analyzed based on that identification. If CD7 is not present, the cell or cells are next interrogated at a fourth level of identification for the presence of CD123, representative of the eighth electrode (2108).

Turning next in FIG. 3 to an embodiment in which a cell population does not express CD7, the cell or cells are next interrogated at a fourth level of identification for the presence of CD123, representative of the eighth electrode (2108). If CD123 is present, the cell population has reached its final point of cell surface phenotyping for the exemplary assay and the cell or cells are identified as dendritic cells (DC) and can be stored in the sixth cell collection reservoir (2206) and further analyzed based on that identification. If CD123 is not present, the cell or cells are next interrogated at a fifth level of identification for the presence of CD20, representative of the ninth electrode (2109).

Turning next in FIG. 3 to an embodiment in which a cell population does not express CD123, the cell or cells are next interrogated at a fifth level of identification for the presence of CD20, representative of the ninth electrode (2109). If CD20 is present, the cell or cells are next interrogated at a sixth level of identification for the presence of LgM, representative of the eleventh electrode (2111). If CD20 is not present, the cell or cells are next interrogated at a sixth level of identification for the presence of CD14, representative of the tenth electrode (2110).

Turning in FIG. 3 to an embodiment in which a cell population expresses CD20, the cell or cells are next interrogated at a sixth level of identification for the presence of LgM, representative of the eleventh electrode (2111). If LgM is present, the cell population has reached its final point of cell surface phenotyping for the exemplary assay and the cell or cells are identified as naïve B cells and can be stored in the eighth cell collection reservoir (2208) and further analyzed based on that identification. If LgM is not present, the cell population has reached its final point of cell surface phenotyping for the exemplary assay and the cell or cells are identified as mature B cells and can be stored in the seventh cell collection reservoir (2207) and further analyzed based on that identification.

Turning in FIG. 3 to an embodiment in which a cell population does not express CD20, the cell or cells are next interrogated at a sixth level of identification for the presence of CD14, representative of the tenth electrode (2110). If CD14 is present, the cell or cells are next interrogated at a seventh level of identification for the presence of HLA-DR, representative of the thirteenth electrode (2113). If CD14 is not present, the cell or cells are next interrogated at a seventh level of identification for the presence of HLA, representative of the twelfth electrode (2112).

Turning next in FIG. 3 to an embodiment in which a cell population expresses CD14, the cell or cells are next interrogated at seventh level of identification for the presence of HLA-DR, representative of the thirteenth electrode (2113). In one embodiment, the presence of HLA-DR can also be quantified, such as through impedance measurements in the thirteenth electrode, and the cells categorized with respect to low, medium, and high levels of HLA-DR antigen presence on the cell or cells. In some embodiments, the level of expression of HLA-DR antigen will be determined by titration. If the cell population expresses high or medium levels of HLA-DR, it has reached its final point of cell phenotyping. If the cell population expresses low levels of HLA-DR, the cell population has reached its final point of cell surface phenotyping for the exemplary assay and the cell or cells are identified as CD14 positive monocytes and can be stored in the tenth cell collection reservoir (2210) and further analyzed based on that identification.

Turning next in FIG. 3 to an embodiment in which a cell population does not express CD14, the cell or cells are next interrogated at seventh level of identification for the presence of HLA, representative of the twelfth electrode (2112). In one embodiment, the presence of HLA can also be quantified, such as through impedance measurements in the twelfth electrode, and the cells categorized with respect to low, medium, and high levels of HLA antigen presence on the cell or cells. If the cell population expresses high or medium levels of HLA, it has reached its final point of cell phenotyping. If the cell population expresses low levels of HLA, the cell population has reached its final point of cell surface phenotyping for the exemplary assay and the cell or cells are identified as CD14 negative monocytes and can be stored in the ninth cell collection reservoir (2209) and further analyzed based on that identification.

The immune assay will be implemented on digital microfluidic devices composed of insulated electrode arrays (FIG. 2). On these electrode arrays, discrete droplets can be manipulated individually in a programmed manner including droplet transport, mixing and merging without the need for mechanical moving parts based on an electrowetting or electromechanical manipulation principle. In this manner, microliter to picoliters of droplets can be manipulated and droplet-based functions can be performed according to real time needs.

The schematic of the implementation of the DMF-based immune assay is shown in FIG. 2.

To further illustrate operation of the assays described herein, reference is made to FIG. 2 and FIG. 3 as part of an illustration of an exemplary embodiment in which a droplet containing a CD4 positive $\alpha\beta$ T cell is interrogated and the cell identified utilizing the assays and methods described herein. In this exemplary embodiment, a droplet (2032) containing a cell or cells can be split from a sample (2031) and manipulated electromechanically to travel downstream away from sample reservoir (2030) along the first channel (2001). The cell or cells in the droplet (2032) can be interrogated for CD45 antigen presence at the first electrode (2101). If positive for CD45, the droplet can be manipulated to move further downstream to the second electrode (2102) where it can be interrogated for CD3 antigen. If CD3 antigen is present, the droplet will be electromechanically manipulated at the first channel junction to move along the second channel, away from the first channel junction and toward the second channel junction. The droplet will then be interrogated at the third electrode for the presence of CD8 antigen. Assuming CD8 is not present, the droplet will be manipulated to move along the fourth channel, away from the second channel junction and toward the third channel junction. Just downstream of the second channel junction and within the fourth channel, the cell or cells in the droplet will be interrogated at the fourth electrode for the presence of CD4 antigen. Assuming CD4 is present, the droplet will be manipulated to move along the fourth channel to the fifth electrode for interrogation of the presence or absence of $\alpha\beta$ antigen. Assuming $\alpha\beta$ is present, the droplet will be manipulated to move along the sixth channel, away from the third channel junction and toward the first cell collection reservoir. The droplet would be considered to contain a cell or cells identified as having a CD4 positive $\alpha\beta$ T cell phenotype, and can be quantified or further analyzed.

In some embodiments, microfluidic devices are provided that is configured to concurrently identify, from a single sample of white blood cells, two or more cell subtypes selected from CD4 positive alpha beta cells, CD4 positive gamma delta cells, CD8 positive alpha beta cells, CD8 positive gamma delta cells, NK cells, mature B cells, naïve B cells, HLA positive cells, HLA-DR positive cells, and dendritic cells. The microfluidic devices can be further configured to quantify the number of cells in each of the two or more cell subtypes. In some embodiments, the microfluidic devices can have three or more electrodes selected from an electrode having immobilized anti-CD45 antibody, an electrode having immobilized anti-CD3 antibody, an electrode having immobilized anti-CD8 antibody, an electrode having immobilized anti-CD4 antibody, an electrode having immobilized anti-$\alpha\beta$ antibody, an electrode having immobilized anti-CD7 antibody, an electrode having immobilized anti-CD123 antibody, an electrode having immobilized anti-CD20 antibody, an electrode having immobilized anti-CD14 antibody, an electrode having immobilized anti-LgM antibody, an electrode having immobilized anti-HLA antibody, and an electrode having immobilized anti-HLA-DR antibody. In some embodiments, the microfluidic devices can be configured to identify the two or more cell subtypes by contacting one or more droplets of the sample with two or more of the electrodes.

The microfluidic devices provided herein can have a channel network including the one or more electrodes, wherein the channel network includes one or more channels in which sample flows from an upstream portion at a sample reservoir to a downstream portion away from the sample reservoir in a downstream direction. In some embodiments, a microfluidic device can include an electrode with immobilized anti-CD45 antibody; an electrode with immobilized anti-CD3 antibody; an electrode with immobilized anti-CD8 antibody; an electrode with immobilized anti-CD4 antibody; and an electrode with immobilized anti-αβ antibody, wherein the electrode with immobilized anti-αβ antibody is downstream of the electrode with immobilized anti-CD4 antibody, the electrode with immobilized anti-CD4 antibody is downstream of the electrode with immobilized anti-CD8 antibody, the electrode with immobilized anti-CD8 antibody is downstream of the electrode with immobilized anti-CD3 antibody, and the electrode with immobilized anti-CD3 antibody is downstream of the electrode with immobilized anti-CD45 antibody.

In some embodiments, a microfluidic device can have an electrode with immobilized anti-CD45 antibody; an electrode with immobilized anti-CD3 antibody; an electrode with immobilized anti-CD8 antibody; and an electrode with immobilized anti-αβ antibody, wherein the electrode with immobilized anti-αβ antibody is downstream of the electrode with immobilized anti-CD8 antibody, the electrode with immobilized anti-CD8 antibody is downstream of the electrode with immobilized anti-CD3 antibody, and the electrode with immobilized anti-CD3 antibody is downstream of the electrode with immobilized anti-CD45 antibody.

In some embodiments, a microfluidic device can have an electrode with immobilized anti-CD45 antibody; an electrode with immobilized anti-CD3 antibody; and an electrode with immobilized anti-CD7 antibody, wherein the electrode with immobilized anti-CD7 antibody is downstream of the electrode with immobilized anti-CD3 antibody, and the electrode with immobilized anti-CD3 antibody is downstream of the electrode with immobilized anti-CD45 antibody.

In some embodiments, a microfluidic device can have an electrode with immobilized anti-CD45 antibody; an electrode with immobilized anti-CD3 antibody; an electrode with immobilized anti-CD7 antibody; and an electrode with immobilized anti-CD123 antibody, wherein the electrode with immobilized anti-CD123 antibody is downstream of the electrode with immobilized anti-CD7 antibody, the electrode with immobilized anti-CD7 antibody is downstream of the electrode with immobilized anti-CD3 antibody, and the electrode with immobilized anti-CD3 antibody is downstream of the electrode with immobilized anti-CD45 antibody.

In some embodiments, a microfluidic device can have an electrode with immobilized anti-CD45 antibody; an electrode with immobilized anti-CD3 antibody; an electrode with immobilized anti-CD7 antibody; an electrode with immobilized anti-CD123 antibody; an electrode with immobilized anti-CD20 antibody; and an electrode with immobilized anti-LgM antibody, wherein the electrode with immobilized anti-LgM antibody is downstream of the electrode with immobilized anti-CD20 antibody, the electrode with immobilized anti-CD20 antibody is downstream of the electrode with immobilized anti-CD123 antibody, the electrode with immobilized anti-CD123 antibody is downstream of the electrode with immobilized anti-CD7 antibody, the electrode with immobilized anti-CD7 antibody is downstream of the electrode with immobilized anti-CD3 antibody, and the electrode with immobilized anti-CD3 antibody is downstream of the electrode with immobilized anti-CD45 antibody.

In some embodiments, a microfluidic device can have an electrode with immobilized anti-CD45 antibody; an electrode with immobilized anti-CD3 antibody; an electrode with immobilized anti-CD7 antibody; an electrode with immobilized anti-CD123 antibody; an electrode with immobilized anti-CD20 antibody; an electrode with immobilized anti-CD14 antibody; and an electrode with immobilized anti-HLA antibody, wherein the electrode with immobilized anti-HLA antibody is downstream of the electrode with immobilized anti-CD14 antibody, the electrode with immobilized anti-CD14 antibody is downstream of the electrode with immobilized anti-CD20 antibody, the electrode with immobilized anti-CD20 antibody is downstream of the electrode with immobilized anti-CD123 antibody, the electrode with immobilized anti-CD123 antibody is downstream of the electrode with immobilized anti-CD7 antibody, the electrode with immobilized anti-CD7 antibody is downstream of the electrode with immobilized anti-CD3 antibody, and the electrode with immobilized anti-CD3 antibody is downstream of the electrode with immobilized anti-CD45 antibody.

In some embodiments, a microfluidic device can have an electrode with immobilized anti-CD45 antibody; an electrode with immobilized anti-CD3 antibody; an electrode with immobilized anti-CD7 antibody; an electrode with immobilized anti-CD123 antibody; an electrode with immobilized anti-CD20 antibody; an electrode with immobilized anti-CD14 antibody; and an electrode with immobilized anti-HLA-DR antibody, wherein the electrode with immobilized anti-HLA-DR antibody is downstream of the electrode with immobilized anti-CD14 antibody, the electrode with immobilized anti-CD14 antibody is downstream of the electrode with immobilized anti-CD20 antibody, the electrode with immobilized anti-CD20 antibody is downstream of the electrode with immobilized anti-CD123 antibody, the electrode with immobilized anti-CD123 antibody is downstream of the electrode with immobilized anti-CD7 antibody, the electrode with immobilized anti-CD7 antibody is downstream of the electrode with immobilized anti-CD3 antibody, and the electrode with immobilized anti-CD3 antibody is downstream of the electrode with immobilized anti-CD45 antibody.

In some embodiments, the assays described herein can include parallel assays. For example, a droplet can be analyzed as part of an assay for identification of cell surface phenotype using the digital microfluidic devices described herein, and a parallel assay for further analyzing one or more of the identified cells, such as RNA analysis, can be conducted on the same cell or cells. In some embodiments, the parallel assays can include, but are not limited to, specific quantification of cells, single cell RNA analysis, and signal transduction by protein quantification. In some embodiments, specific quantification of cells can be achieved through cell surface immune phenotyping and impedance measurement on one or more electrodes of the digital microfluidic devices described here. In some embodiments, single cell RNA analysis can be conducted by whole RNA sequencing or microarray. In some embodiments, signal transduction can be analyzed by protein quantification of proteins capable of passing through a synthetic nuclear membrane.

In some embodiments, parallel assays can be conducted entirely on the digital microfluidic devices described herein. For example, cell surface phenotyping and quantification can be conducted together on the same digital microfluidic device. In some embodiments, parallel assays will be conducted one different devices. For example, cell surface phenotyping can be conducted on a digital microfluidic device as described herein. Upon identifying and grouping one or more cell surface phenotypes, one or more cell subpopulations sorted by the digital microfluidic device can be removed from the digital microfluidic device and analyzed further in a parallel assay. In some embodiments, cell surface phenotyping includes both identifying cell surface markers and quantifying cells and/or cell surface markers. In some embodiments, once a cell has reached its final point of cell surface phenotyping (e.g., quantification and identification), it can be lysed and its protein can be separated from RNA. In some embodiments, techniques for separating the RNA and protein content of the cell or cells include, but are not limited to, using specific chemical reagents, filtration, or electrostatic force. In some embodiments, RNA can be analyzed using either genome wide RNA sequencing or standard PCR techniques for microarray analysis of targeted genes. In some embodiments, proteins can be filtered through a synthetic nuclear membrane. In some embodiments, a synthetic nuclear membrane can include, but is not limited to artificial cells, liposomes, polymersomes, and microcapsules. In some embodiments, encapsulated proteins within the artificial nucleus can be analyzed using standard mass spectrometry to identify active signal transduction pathways.

In some embodiments, a method is provided for determining the immunological phenotype of a plurality of white blood cells in a sample including: (a) introducing the sample having a plurality of white blood cells into a sample reservoir of a microfluidic device; (b) dispensing, by electromechanical droplet manipulation, a droplet of the sample including a cell from the sample reservoir into a channel operably connected to the sample reservoir; (c) moving the droplet, by electromechanical droplet manipulation, along the channel to a first immobilization electrode; (d) determining whether or not the cell is immobilized on the first immobilization electrode; (e) determining the cell's subtype based on step (d); (f)

moving the droplet including the cell, by electromechanical droplet manipulation, from the first immobilization electrode along a channel in a direction based on the cell's subtype determined in step (d); (g) determining the cell's final phenotypic subtype; and (h) moving the droplet including the cell, by electromechanical droplet manipulation, along a channel to a cell collection reservoir based on the cell's final phenotypic subtype determined in step (g). In some embodiments, the method can further include (i) repeating steps (b)-(h). Steps (b)-(h) can be repeated until some or all of the cells in the sample have been phenotyped. In some embodiments of the method, step (g) can include determining whether or not the cell is immobilized on one or more immobilization electrodes. In some embodiments, the one or more immobilization electrodes are selected from an electrode having immobilized anti-CD45 antibody, an electrode having immobilized anti-CD3 antibody, an electrode having immobilized anti-CD8 antibody, an electrode having immobilized anti-CD4 antibody, an electrode having immobilized anti-αβ antibody, an electrode having immobilized anti-CD7 antibody, an electrode having immobilized anti-CD123 antibody, an electrode having immobilized anti-CD20 antibody, an electrode having immobilized anti-CD14 antibody, an electrode having immobilized anti-LgM antibody, an electrode having immobilized anti-HLA antibody, and an electrode having immobilized anti-HLA-DR antibody. In some embodiments, step (g) can include determining a cell subtype selected from CD4 positive alpha beta cells, CD4 positive gamma delta cells, CD8 positive alpha beta cells, CD8 positive gamma delta cells, NK cells, mature B cells, naïve B cells, HLA positive cells, HLA-DR positive cells, and dendritic cells. The method can further include concurrently identifying two or more cell subtypes selected from CD4 positive alpha beta cells, CD4 positive gamma delta cells, CD8 positive alpha beta cells, CD8 positive gamma delta cells, NK cells, mature B cells, naïve B cells, HLA positive cells, HLA-DR positive cells, and dendritic cells. The method can be carried out on any of the microfluidic devices described herein.

The method can, in some embodiments, further include (j) independently collecting cells of one or more subtypes to create one or more pools of cells having the same subtype. The cells in the one or more pools of cells having the same subtype can be lysed in a step (k) to release cellular contents. The lysing can be conducted within a cell collection reservoir on a microfluidic device, or the cells can first be extracted from a microfluidic device by way of an outlet port and lysed outside of the microfluidic device. The method can further include (1) analyzing the cellular contents of the lysed cells, which can include, for example, separating the cellular contents into an RNA component and a cellular protein component and analyzing a component selected from the RNA component and the cellular protein component. Analysis can be conducted within the microfluidic device, or the cellular contents can be analyzed on other devices outside of the microfluidic device. Analyzing the cellular protein component can include passing the cellular protein component through a filter, such as, for example a synthetic nuclear membrane. In some embodiments, the filter can be an artificial cell, a liposome, a polymersome, or a microfilter. Analyzing the RNA component can include, for example, conducting genome wide RNA sequencing, or PCR microarray analysis of target genes. Other conventional methods of protein analysis and RNA analysis can be utilized in the methods.

In some embodiments, a method of analyzing, independently, the RNA of a single cell subtype in a sample having a plurality of cell subtypes is provided. The method can include (a) splitting the sample into one or more cell subtypes by passing at least a portion of the sample through a digital microfluidic device to create one or more pools of cells having the same subtype; (b) lysing one or more pools of cells having the same subtype to release cellular contents; (c) separating the cellular contents into an RNA component and a cellular protein component; and (d) analyzing the RNA component. The methods can be conducted using the microfluidic devices described herein.

In some embodiments, a method of analyzing signal transduction proteins of a single cell subtype in a sample having a plurality of cell subtypes is provided. The method can include (a) splitting the sample into one or more cell subtypes by passing at least a portion of the sample through a digital microfluidic device to create one or more pools of cells having the same subtype; (b) lysing one or more pools of cells having the same subtype to release cellular contents; (c) separating the cellular contents into an RNA component and a cellular protein component; and (d) analyzing the cellular protein component. The methods can be conducted using the microfluidic devices described herein.

In some embodiments, a method of determining the disease phenotype of an immune mediated disease in a patient having the immune mediated disease is provided, including (a) splitting the sample into one or more cell subtypes by passing at least a portion of the sample through a digital microfluidic device to create one or more pools of cells having the same subtype; (b) lysing one or more pools of cells having the same subtype to release cellular contents; (c) separating the cellular contents into an RNA component and a cellular protein component; (d) analyzing at least one of the RNA component and the cellular protein component; and (e) determining the disease phenotype based on step (d).

In some embodiments, the immune mediated disease can be selected from Crohn's disease, multiple sclerosis, rheumatoid arthritis, and inflammatory bowel disease. In some embodiments, the immune mediated disease is Crohn's disease and wherein the disease phenotype is selected from severe Crohn's disease and indolent Crohn's disease. Crohn's disease can be characterized as severe or indolent based on a medical professional's analysis of a patient's symptoms, levels of inflammation markers such as C Reactive Protein (CRP) in the blood, medical imaging results, history (e.g., age of onset, number of surgeries), the location of the inflammation, and radiographic and endoscopic features. Information at the level of the single cell (gene expression, signal transduction), as achieved through the methods and devices described herein, may be correlated with current techniques of identifying severity (e.g. symptoms, imaging, CRP levels, endoscopy), and may provide insight into the prediction of response to particular therapeutics or disease prognosis. In some embodiments, the immune mediated disease is Rheumatoid Arthritis. Information at the level of the single cell (gene expression, signal transduction), as achieved through the methods and devices described herein, may be correlated with current techniques of identifying severity (e.g. joint destruction as recorded on X-ray), and may provide insight into the prediction of response to particular therapeutics or disease prognosis. The methods can be conducted using the microfluidic devices described herein.

In some embodiments, a method of determining the immunological phenotype of a plurality of white blood cells in a sample is provided. The method can include (a) identifying a cell subtype for each of two or more of the white blood cells; (b) quantifying each cell subtype; (c) isolating and pooling cells of each subtype into one or more subtype pools; (d) lysing cells of each of the one or more subtype pools to yield one or more cellular content pools; (e) separating the cellular content pools of each cell subtype into an RNA component and a protein component; and (f) analyzing at least one of the RNA component and the protein component. In some embodiments of the method, step (a) can include moving one or more droplets of the sample through a channel network of a microfluidic device. In some embodiments, step (a) can include moving one or more droplets of the sample through a microfluidic device selected from the microfluidic device of claim 19, the microfluidic device of claim 26, and the microfluidic device of claim 38.

number of embodiments of the invention have been described. Nevertheless, it will be understood that various modifications may be made without departing from the spirit and scope of the invention. For example, different antibodies can be immobilized on the electrodes, or the electrodes can be arranged in different orders with respect to the downstream flow of sample, such that other types of disease can be phenotyped and analyzed. Accordingly, other embodiments are within the scope of the following claims.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining an immunological phenotype of a plurality of white blood cells in a sample comprising:
   (a) introducing a sample comprising a plurality of white blood cells into a sample reservoir of a microfluidic device;
   (b) dispensing, by electromechanical droplet manipulation, a droplet of said sample comprising a cell from said sample reservoir into a channel operably connected to said sample reservoir;
   (c) moving said droplet, by electromechanical droplet manipulation, along said channel to a first immobilization electrode;
   (d) determining whether or not said cell is immobilized on said first immobilization electrode;
   (e) determining a subtype of said cell based on step (d);
   (f) moving said droplet comprising said cell, by electromechanical droplet manipulation, from said first immobilization electrode along a channel in a direction based on said subtype of said cell determined in step (d);
   (g) determining a final phenotypic subtype of said cell; and
   (h) moving said droplet comprising said cell, by electromechanical droplet manipulation, along a channel to a cell collection reservoir based on such final phenotypic subtype of said cell determined in step (g).

2. The method of claim 1, further comprising:
   (i) repeating steps (b)-(h) for a second droplet of said sample, wherein said second droplet comprises a cell.

3. The method of claim 1, wherein step (g) comprises determining whether or not said cell is immobilized on one or more immobilization electrodes.

4. The method of claim 3, wherein said one or more immobilization electrodes are selected from an electrode comprising immobilized anti-CD45 antibody, an electrode comprising immobilized anti-CD3 antibody, an electrode comprising immobilized anti-CD8 antibody, an electrode comprising immobilized anti-CD4 antibody, an electrode comprising immobilized anti-$\alpha\beta$ antibody, an electrode comprising immobilized anti-CD7 antibody, an electrode comprising immobilized anti-CD123 antibody, an electrode comprising immobilized anti-CD20 antibody, an electrode comprising immobilized anti-CD14 antibody, an electrode comprising immobilized anti-LgM antibody, an electrode comprising immobilized anti-HLA antibody, and an electrode comprising immobilized anti-HLA-DR antibody.

5. The method of claim 1, wherein step (g) comprises determining a cell subtype selected from CD4 positive alpha beta cells, CD4 positive gamma delta cells, CD8 positive alpha beta cells, CD8 positive gamma delta cells, NK cells-, mature B cells, naïve B cells, HLA positive cells, HLA-DR positive cells, and dendritic cells.

6. The method of claim 2, comprising concurrently identifying two or more cell subtypes selected from CD4 positive alpha beta cells, CD4 positive gamma delta cells, CD8 positive alpha beta cells, CD8 positive gamma delta cells, NK cells, mature B cells, naïve B cells, HLA positive cells, HLA-DR positive cells, and dendritic cells.

7. The method of claim 1, further comprising:
   (j) independently collecting cells of one or more subtypes to create one or more pools of cells having the same subtype.

8. The method of claim 1, further comprising:
   (k) lysing one or more pools of cells having the same subtype to release cellular contents.

9. The method of claim 8, further comprising:
   (l) analyzing said cellular contents.

10. The method of claim 9, wherein analyzing said cellular contents comprises separating said cellular contents into an RNA component and a cellular protein component.

11. A microfluidic device configured to concurrently identify, from a single sample of white blood cells, two or more cell subtypes selected from CD4 positive alpha beta cells, CD4 positive gamma delta cells, CD8 positive alpha beta cells, CD8 positive gamma delta cells, NK cells, mature B cells, naïve B cells, HLA positive cells, HLA-DR positive cells, and dendritic cells, wherein said device comprises three or more electrodes selected from an electrode comprising immobilized anti-CD45 antibody, an electrode comprising immobilized anti-CD3 antibody, an electrode comprising immobilized anti-CD8 antibody, an electrode comprising immobilized anti-CD4 antibody, an electrode comprising immobilized anti-αβ antibody, an electrode comprising immobilized anti-CD7 antibody, an electrode comprising immobilized anti-CD123 antibody, an electrode comprising immobilized anti-CD20 antibody, an electrode comprising immobilized anti-CD14 antibody, an electrode comprising immobilized anti-LgM antibody, an electrode comprising immobilized anti-HLA antibody, and an electrode comprising immobilized anti-HLA-DR antibody, wherein said microfluidic device comprises a channel network comprising said one or more electrodes, wherein said channel network comprises one or more channels in which sample flows from an upstream portion at a sample reservoir to a downstream portion away from said sample reservoir in a downstream direction, wherein:

(a) said microfluidic device comprises:
an electrode comprising immobilized anti-CD45 antibody;
an electrode comprising immobilized anti-CD3 antibody;
an electrode comprising immobilized anti-CD8 antibody;
an electrode comprising immobilized anti-CD4 antibody; and
an electrode comprising immobilized anti-αβ antibody,
wherein said electrode comprising immobilized anti-αβ antibody is downstream of said electrode comprising immobilized anti-CD4 antibody, said electrode comprising immobilized anti-CD4 antibody is downstream of said electrode comprising immobilized anti-CD8 antibody, said electrode comprising immobilized anti-CD8 antibody is downstream of said electrode comprising immobilized anti-CD3 antibody, and said electrode comprising immobilized anti-CD3 antibody is downstream of said electrode comprising immobilized anti-CD45 antibody;

(b) said microfluidic device comprises:
an electrode comprising immobilized anti-CD45 antibody;
an electrode comprising immobilized anti-CD3 antibody; and
an electrode comprising immobilized anti-CD7 antibody,
wherein said electrode comprising immobilized anti-CD7 antibody is downstream of said electrode comprising immobilized anti-CD3 antibody, and said electrode comprising immobilized anti-CD3 antibody is downstream of said electrode comprising immobilized anti-CD45 antibody;

(c) said microfluidic device comprises:
an electrode comprising immobilized anti-CD45 antibody;
an electrode comprising immobilized anti-CD3 antibody;
an electrode comprising immobilized anti-CD7 antibody; and
an electrode comprising immobilized anti-CD123 antibody,
wherein said electrode comprising immobilized anti-CD123 antibody is downstream of said electrode comprising immobilized anti-CD7 antibody, said electrode comprising immobilized anti-CD7 antibody is downstream of said electrode comprising immobilized anti-CD3 antibody, and said electrode comprising immobilized anti-CD3 antibody is downstream of said electrode comprising immobilized anti-CD45 antibody, (d) said microfluidic device comprises:
an electrode comprising immobilized anti-CD45 antibody;
an electrode comprising immobilized anti-CD3 antibody;
an electrode comprising immobilized anti-CD7 antibody;
an electrode comprising immobilized anti-CD123 antibody;
an electrode comprising immobilized anti-CD20 antibody; and
an electrode comprising immobilized anti-LgM antibody,
wherein said electrode comprising immobilized anti-LgM antibody is downstream of said electrode comprising immobilized anti-CD20 antibody, said electrode comprising immobilized anti-CD20 antibody is downstream of said electrode comprising immobilized anti-CD123 antibody, said electrode comprising immobilized anti-CD123 antibody is downstream of said electrode comprising immobilized anti-CD7 antibody, said electrode comprising immobilized anti-CD7 antibody is downstream of said electrode comprising immobilized anti-CD3 antibody, and said electrode comprising immobilized anti-CD3 antibody is downstream of said electrode comprising immobilized anti-CD45 antibody;

(e) said microfluidic device comprises:
an electrode comprising immobilized anti-CD45 antibody;
an electrode comprising immobilized anti-CD3 antibody;
an electrode comprising immobilized anti-CD7 antibody;
an electrode comprising immobilized anti-CD123 antibody;
an electrode comprising immobilized anti-CD20 antibody;
an electrode comprising immobilized anti-CD14 antibody; and
an electrode comprising immobilized anti-HLA antibody,
wherein said electrode comprising immobilized anti-HLA antibody is downstream of said electrode comprising immobilized anti-CD14 antibody, said electrode comprising immobilized anti-CD14 antibody is downstream of said electrode comprising immobilized anti-CD20 antibody, said electrode comprising immobilized anti-CD20 antibody is downstream of said electrode comprising immobilized anti-CD123 antibody, said electrode comprising immobilized anti-CD123 antibody is downstream of said electrode comprising immobilized anti-CD7 antibody, said electrode comprising immobilized anti-CD7 antibody is downstream of said electrode comprising immobilized anti-CD3 antibody, and said electrode comprising immobilized anti-CD3 antibody is downstream of said electrode comprising immobilized anti-CD45 antibody; or (f) said microfluidic device comprises:
an electrode comprising immobilized anti-CD45 antibody;
an electrode comprising immobilized anti-CD3 antibody;
an electrode comprising immobilized anti-CD7 antibody;
an electrode comprising immobilized anti-CD123 antibody;
an electrode comprising immobilized anti-CD20 antibody;
an electrode comprising immobilized anti-CD14 antibody; and
an electrode comprising immobilized anti-HLA-DR antibody,
wherein said electrode comprising immobilized anti-HLA-DR antibody is downstream of said electrode comprising immobilized anti-CD14 antibody, said electrode comprising immobilized anti-CD14 antibody is downstream of said electrode comprising immobilized anti-CD20 antibody, said electrode comprising immobilized anti-CD20 antibody is downstream of said electrode comprising immobilized anti-CD123 antibody, said electrode comprising immobilized anti-CD123 antibody is downstream of said electrode comprising immobilized anti-CD7 antibody, said electrode comprising immobilized anti-CD7 antibody is downstream of said electrode comprising immobilized anti-CD3 antibody, and said electrode comprising immobilized anti-CD3 antibody is downstream of said electrode comprising immobilized anti-CD45 antibody.

12. The microfluidic device of claim 11, further configured to quantify the number of cells in each of said two or more cell subtypes.

13. The microfluidic device of claim 11, wherein said device is configured to identify said two or more cell subtypes by contacting one or more droplets of said sample with two or more of said electrodes.

14. The microfluidic device of claim 11, wherein said microfluidic device comprises said (a).

15. The microfluidic device of claim 14 comprising:
an electrode comprising immobilized anti-CD45 antibody;
an electrode comprising immobilized anti-CD3 antibody;
an electrode comprising immobilized anti-CD8 antibody; and
an electrode comprising immobilized anti-αβ antibody,
wherein said electrode comprising immobilized anti-αβ antibody is downstream of said electrode comprising immobilized anti-CD8 antibody, said electrode comprising immobilized anti-CD8 antibody is downstream of said electrode comprising immobilized anti-CD3 antibody, and said electrode comprising immobilized anti-CD3 antibody is downstream of said electrode comprising immobilized anti-CD45 antibody.

16. The microfluidic device of claim 11, wherein said microfluidic device comprises said (b).

17. The microfluidic device of claim 11, wherein said microfluidic device comprises said (c).

18. The microfluidic device of claim 11, wherein said microfluidic device comprises said (d).

19. The microfluidic device of claim 11, wherein said microfluidic device comprises said (e).

20. The microfluidic device of claim 11, wherein said microfluidic device comprises said (f).

\* \* \* \* \*